United States Patent [19]

Ravichandran et al.

[11] Patent Number: 5,554,754

[45] Date of Patent: Sep. 10, 1996

[54] AZODICARBOXYLIC ACID DERIVATIVES CONTAINING HINDERED AMINE MOIETIES AS POLYMER STABILIZERS

[75] Inventors: Ramanathan Ravichandran, Nanuet; Ambelal R. Patel, Scarsdale, both of N.Y.

[73] Assignee: Ciba-Geigy Corporation, Tarrytown, N.Y.

[21] Appl. No.: 463,453

[22] Filed: Jun. 5, 1995

Related U.S. Application Data

[60] Division of Ser. No. 316,272, Sep. 30, 1994, Pat. No. 5,470,980, which is a continuation-in-part of Ser. No. 224,616, Apr. 7, 1994, Pat. No. 5,380,828, which is a continuation-in-part of Ser. No. 132,081, Oct. 5, 1993, abandoned.

[51] Int. Cl.$^6$ ............................. C07D 211/00; C08K 5/34
[52] U.S. Cl. .................... 546/184; 546/188; 546/190; 524/99; 524/102; 534/732; 534/751
[58] Field of Search .................... 546/190, 188, 546/184; 534/732, 751; 524/99, 102

[56] References Cited

U.S. PATENT DOCUMENTS

| | | |
|---|---|---|
| 3,655,391 | 4/1992 | Merli et al. . |
| 4,153,596 | 5/1979 | Oertel et al. . |
| 4,223,147 | 9/1980 | Oertel et al. ............................. 546/190 |
| 4,255,536 | 3/1981 | Udipi . |
| 4,927,891 | 5/1990 | Kamath et al. ........................ 525/327.3 |
| 5,021,480 | 6/1991 | Ravichandran . |
| 5,041,545 | 8/1991 | Myers . |
| 5,116,976 | 5/1992 | Myers ........................................ 546/20 |
| 5,204,473 | 4/1993 | Winter et al. . |
| 5,233,047 | 8/1993 | MacLeay et al. . |
| 5,338,853 | 8/1994 | MacLeay et al. ........................ 546/190 |
| 5,380,828 | 1/1995 | Ravichandran et al. ................ 546/190 |

FOREIGN PATENT DOCUMENTS

| | | |
|---|---|---|
| 303987 | 2/1989 | European Pat. Off. . |
| 389429 | 9/1990 | European Pat. Off. . |
| 0467344 | 1/1992 | European Pat. Off. . |
| 2642446 | 3/1978 | Germany . |

OTHER PUBLICATIONS

Chem. Abst. 89:431252 of DE 2642,446.
S. S. Ivanov, et al., Rubber Chem. & Tech., 30, 895 (1957).
D. S. Campbell et al., Polymer 20:393 (1979).
D. N. Schulz et al., Macromolecules 13, 1967 (1980).

*Primary Examiner*—Shean C. Wu
*Attorney, Agent, or Firm*—Michele A. Kovaleski

[57] ABSTRACT

New azodicarboxylic acid derivatives of formula I

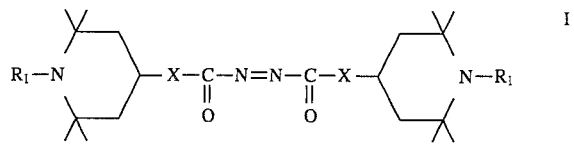

where $R_1$ is hydrogen, oxyl, hydroxyl, alkyl, allyl, benzyl, alkoxy or acyl, and X is —O— or —NR— where R is hydrogen or alkyl, are useful for the stabilization of polymers, particularly unsaturated elastomers, by being grafted thereon.

15 Claims, No Drawings

AZODICARBOXYLIC ACID DERIVATIVES CONTAINING HINDERED AMINE MOIETIES AS POLYMER STABILIZERS

This is a divisional of Ser. No. 08/316,272, filed Sep. 30, 1994 now U.S. Pat. No. 5,470,980, which is a continuation in part of Ser. No. 08/224,616, filed Apr. 7, 1994; now U.S. Pat. No. 5,380,828, which is a continuation in part of Ser. No. 08/132,081, filed Oct. 5, 1993, now abandoned.

The instant invention pertains to novel azodicarboxylic acid derivatives and to polymer compositions stabilized therewith.

BACKGROUND OF THE INVENTION

U.S. Pat. No. 4,255,536 teaches that selected azodicarboxylates are useful to modify copolymers containing residual unsaturation.

S. S. Ivanov et al. disclose in Rubber Chem. and Tech., 30, 895 (1957) the reaction of azodicarboxylates with rubber to form branched and crosslinked derivatives.

D. S. Campbell et al., Polymer 19, 1107 (1978) and Polymer 20, 393 (1979) disclose the efficient grafting of polystyrene containing reactive azodicarboxylate units onto polydienes both in solution and in the absence of a solvent.

D. N. Schulz et al., Macromolecules 13, 1367 (1980) describe the azodicarboxylate modification of polybutadienes with respect to structure reactivity and structure property relationships.

On the other hand, the potential use of a light stabilizer containing an azodicarboxylic acid derivative to modify unsaturated elastomers and thereby incorporating the light stabilizer into the vulnerable unsaturated backbone of polymers such as ABS, impact polystyrene (IPS), high impact polystyrene (HIPS), SBS, SIS, polybutadiene (PB), polyisoprene (PI), emulsion SBR, EPDM, AES and ASA is not implied in any of the above references. The resulting polymers containing the light stabilizer exhibit greatly improved light stability.

Rubber modified polymers such as ABS and HIPS and several thermoplastics such as polypropylene (PP)/EPDM, PP/NBR, PP/NR and the like are susceptible to light induced oxidative degradation attributed mainly to the unsaturated diene phase. The instant invention locates the light stabilizer in the vulnerable diene phase through a covalent bond via the thermalene reaction of these polymers with compounds of the instant invention. The additive grafts to the polymer backbone during a reactive processing step. In addition to improved light stability, binding of the additive during processing imparts a high degree of permanence. The physical loss of stabilizer additive and migration of said additive is thus minimized during demanding end-use application. Also, non-migrating polymer-bound stabilizer additive can find use in medical and other applications requiting FDA regulation (such as in materials coming into contract with food). Thus, decreased volatility and diffusion and extraction resistance are desirable properties resulting from additives which are grafted onto a substrate.

In alloys and blends such as ABS/polycarbonate (PC), the location of the stabilizer containing a grafted hindered amine light stabilizer moiety only in the ABS phase would prevent its migration to PC where it is highly detrimental. Similar advantages could be foreseen in other polymer blends containing one or more components having unsaturated double bonds present. Examples of such polymer blends are EPDM/PP, NBR/PP, NP/PP, NR/polyphenylene oxide (PPO), emulsion SBR, ABS/nylon, ABS/PVC, ABS/polyester and the like.

OBJECTS OF THE INVENTION

One object of the instant invention is to provide new azodicarboxylic acid derivatives.

Another object of the invention is to provide novel asymmetrical azo derivatives.

Still another object of the invention is to provide stabilized polymer compositions stabilized by the presence of said azodicarboxylic acid derivative and/or said asymmetrical azo derivative.

Still yet another object is to provide new hydrazine derivatives useful as hindered amine stabilizers.

DETAILED DISCLOSURE

The instant invention pertains to an azodicarboxylic acid derivative of formula I

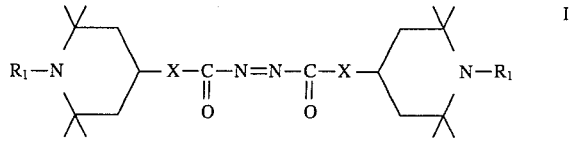

where $R_1$ is hydrogen, oxyl, hydroxyl, alkyl of 1 to 8 carbon atoms, alkyl of 2 to 4 carbon atoms substituted by one hydroxyl group, allyl, benzyl, benzyl substituted by one of two alkyl of 1 to 4 carbon atoms, alkoxy of 1 to 18 carbon atoms, cycloalkoxy of 5 to 12 carbon atoms or alkanoyl of 1 to 8 carbon atoms, and X is —O— or —NR$_2$— where $R_2$ is hydrogen, alkyl of 1 to 18 carbon atoms, cycloalkyl of 5 to 12 carbon atoms, phenylalkyl of 7 to 15 carbon atoms, alkyl of 2 to 4 carbon atoms substituted by one alkoxy group of 1 to 12 carbon atoms or a group of formula II

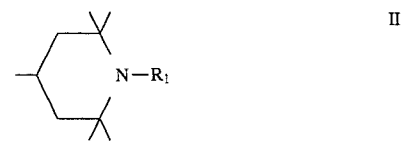

in which $R_1$ is as defined above.

Preferably, $R_1$ is alkyl of 1 to 4 carbon atoms, alkyl of 2 or 3 carbon atoms substituted by one hydroxyl group, alkoxy of 1 to 12 carbon atoms, cycloalkoxy of 5 or 6 carbon atoms or alkanoyl of 1 to 4 carbon atoms.

Preferably, X is —O— or —NR$_2$— where $R_2$ is hydrogen, butyl or dodecyl or a group of formula II.

Most preferably, $R_1$ is methyl, 2-hydroxyethyl, methoxy, heptyloxy, octyloxy, cyclohexyloxy, formyl or acetyl.

Most preferably, X is —O—.

When any of $R_1$ or $R_2$ is or is a group substituted by alkyl, such alkyl groups are, for example, methyl, ethyl, isopropyl, n-butyl, tert-butyl, tert-amyl, 2-ethylhexyl, n-octyl, lauryl, n-tetradecyl, n-octadecyl or eicosyl; when said radicals are cycloalkyl, they are, for example, cyclopentyl, cyclohexyl, cyclooctyl or cyclododecyl; when said radicals are phenylalkyl, they are, for example, benzyl, phenethyl, α-methylbenzyl, α,α-dimethylbenzyl; when said radicals are alkoxy or cycloalkoxy, they are, for example, methoxy, butyloxy, amyloxy, heptyloxy, octyloxy, nonyloxy, dodecyloxy, octadecyloxy, cyclopentyloxy or cyclohexyloxy; when said radicals are hydroxyalkyl or alkoxyalkyl, they are, for example, 2-hydroxyethyl, 2-hydroxypropyl, 3-hydroxypropyl, 2-ethyloxyethyl, 2-butyloxyethyl; when $R_1$ is alkanoyl, it is, for example, formyl, acetyl, propionyl, butyryl, valeroyl, caproyl or caprylyl.

The instant compounds are prepared in a two-step sequence. In the first step, an appropriate 1-substituted 4-amino-, 4-alkylamino- or 4-hydroxy-2,2,6,6-tetramethylpiperidine is convened into the corresponding hydrazine dicarboxylic acid diamide or hydrazine dicarboxylic acid diester derivative. This conversion is accomplished either by a transesterification reaction of the hindered amine with dimethylhydrazine dicarboxylate or by the reaction of chloroformic ester or amide (prepared from a hindered amine derivative and phosgene) with hydrazine hydrate.

In the second step, the hydrazine dicarboxylic acid diester or diamide is oxidized to prepare the instant compounds, namely azodicarboxylic acid esters and amides. Among the oxidizing agents which can be employed are fuming nitric acid, lead peroxide in cold dilute sulfufic acid, lead tetraacetate, t-butylhypochlorite, manganese dioxide, calcium hypochlorite, N-bromosuccinimide, nitrogen tetroxide and iodobenzene diacetate.

The instant invention also pertains to a stabilized polymer composition which comprises (a) a polymer, copolymer or polymer blend which contains in at least one polymer or polymer component significant ethylenic unsaturation, and (b) an effective stabilizing amount of an azodicarboxylic acid derivative grafted to said polymer or polymer component, said derivative having before grafting the structure of formula I

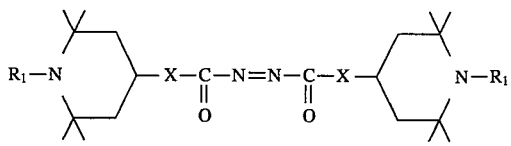

where $R_1$ is hydrogen, oxyl, hydroxyl, alkyl of 1 to 8 carbon atoms, alkyl of 2 to 4 carbon atoms substituted by one hydroxyl group, allyl, benzyl, benzyl substituted by one of two alkyl of 1 to 4 carbon atoms, alkoxy of 1 to 18 carbon atoms, cycloalkoxy of 5 to 12 carbon atoms or alkanoyl of 1 to 8 carbon atoms, and X is —O— or —NR$_2$— where $R_2$ is hydrogen, alkyl of 1 to 18 carbon atoms, cycloalkyl of 5 to 12 carbon atoms, phenylalkyl of 7 to 15 carbon atoms, alkyl of 2 to 4 carbon atoms substituted by one alkoxy group of 1 to 12 carbon atoms or a group of formula II

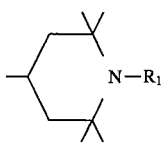

in which $R_1$ is as defined above.

Additionally, the intermediate hydrazine derivatives of formula III

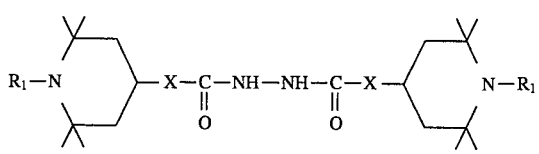

where $R_1$ is hydrogen, oxyl, hydroxyl, alkyl of 1 to 8 carbon atoms, alkyl of 2 to 4 carbon atoms substituted by one hydroxyl group, allyl, benzyl, benzyl substituted by one of two alkyl of 1 to 4 carbon atoms or alkanoyl of 1 to 8 carbon atoms, and X is —O— or —NR$_2$— where $R_2$ is hydrogen, alkyl of 1 to 18 carbon atoms, cycloalkyl of 5 to 12 carbon atoms, phenylalkyl of 7 to 15 carbon atoms, alkyl of 2 to 4 carbon atoms substituted by one alkoxy group of 1 to 12 carbon atoms or a group of formula II

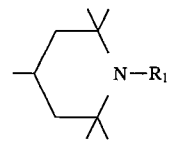

in which $R_1$ is as defined above.

Some compounds of general formula III are described in U.S. Pat. No. 5,204,473 where the N-atom of the piperidine moiety is substituted by an alkoxy, cycloalkoxy, alkenoxy or similar group.

Further, the instant invention relates to asymmetrical compounds which are azo derivatives of formula IV

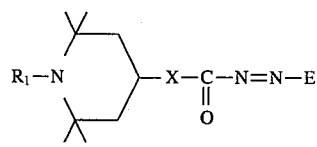

where $R_1$ is hydrogen, oxyl, hydroxyl, alkyl of 1 to 8 carbon atoms, alkyl of 2 to 4 carbon atoms substituted by one hydroxyl group, allyl, benzyl, benzyl substituted by one of two alkyl of 1 to 4 carbon atoms, alkoxy of 1 to 18 carbon atoms, cycloalkoxy of 5 to 12 carbon atoms or alkanoyl of 1 to 8 carbon atoms;

X is —O— or —NR$_2$— where $R_2$ is hydrogen, alkyl of 1 to 18 carbon atoms, cycloalkyl of 5 to 12 carbon atoms, phenylalkyl of 7 to 15 carbon atoms, alkyl of 2 to 4 carbon atoms substituted by one alkoxy group of 1 to 12 carbon atoms or a group of formula II

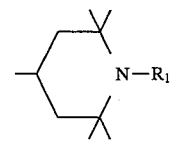

in which $R_1$ is as defined above; and

E is a substituted or unsubstituted alkyl of 1 to 20 carbon atoms, substituted or unsubstituted cycloalkyl of 5 to 12 carbon atoms, substituted or unsubstituted aryl of 6 to 14 carbon atoms or phenylalkyl of 7 to 22 carbon atoms, or E is —CONHR$_4$, —CSNHR$_5$, —COR$_6$COR$_7$, —COR$_8$CONHR$_9$, —COR$_{10}$, —COOR$_{11}$ or —SO$_2$R$_{12}$, in which $R_4$, $R_5$, $R_7$, $R_9$, $R_{10}$, $R_{11}$ and $R_{12}$ are each independently of the other hydrogen, substituted or unsubstituted alkyl of 1 to 20 carbon atoms, substituted or unsubstituted cycloalkyl of 5 to 12 carbon atoms, substituted or unsubstituted aryl of 6 to 14 carbon atoms or phenylalkyl of 7 to 22 carbon atoms; and $R_6$ and $R_8$ are each independently of the other a substituted or unsubstituted alkylene of 1 to 12 carbons.

Preferably, $R_1$ is alkyl of 1 to 4 carbon atoms, alkyl of 2 or 3 carbon atoms substituted by one hydroxyl group, alkoxy of 1 to 12 carbon atoms, cycloalkoxy of 5 or 6 carbon atoms or alkanoyl of 1 to 4 carbon atoms. Most preferably, $R_1$ is methyl, 2-hydroxyethyl, methoxy, heptyloxy, octyloxy, cyclohexyloxy, formyl or acetyl.

Preferably, X is —O— or —$NR_2$— where $R_2$ is hydrogen, butyl or dodecyl or a group of formula II. Most preferably, X is —O—.

When any of $R_1$ or $R_2$ is or is a group substituted by alkyl, such alkyl groups are, for example, methyl, ethyl, isopropyl, n-butyl, tert-butyl, tert-amyl, 2-ethylhexyl, n-octyl, lauryl, n-tetradecyl, n-octadecyl or eicosyl; when said radicals are cycloalkyl, they are, for example, cyclopentyl, cyclohexyl, cyclooctyl or cyclododecyl; when said radicals are phenylalkyl, they are, for example, benzyl, phenethyl, α-methylbenzyl, α,α-dimethylbenzyl; when said radicals are alkoxy or cycloalkoxy, they are, for example, methoxy, butyloxy, amyloxy, heptyloxy, octyloxy, nonyloxy, dodecyloxy, octadecyloxy, cyclopentyloxy or cyclohexyloxy; when said radicals are hydroxyalkyl or alkoxyalkyl, they are, for example, 2-hydroxyethyl, 2-hydroxypropyl, 3-hydroxypropyl, 2-ethyloxyethyl, 2-butyloxyethyl; when $R_1$ is alkanoyl, it is, for example, formyl, acetyl, propionyl, butyryl, valeroyl, caproyl or caprylyl.

Preferably, when E is alkyl, cycloalkyl, aryl or phenylalkyl, E is a substituted or unsubstituted alkyl of 1 to 12 carbon atoms, substituted or unsubstituted cycloalkyl of 5 to 8 carbon atoms, substituted or unsubstituted phenyl, or substituted or unsubstituted phenylalkyl of 7 to 14 carbon atoms. Most preferably, E is a substituted or unsubstituted alkyl of 1 to 10 carbon atoms, substituted or unsubstituted cylohexyl, substituted or unsubstituted phenyl, or phenylalkyl of 7 to 9 carbon atoms.

Preferably, when E is —$CONHR_4$ or —$CSNHR_5$, $R_4$ and $R_5$ each independently of the other are a substituted or unsubstituted alyl of 1 to 12 carbon atoms, substituted or unsubstituted cycloalkyl of 5 to 8 carbon atoms, substituted or unsubstituted phenyl, or substituted or unsubstituted or unsubstituted phenylalkyl of 7 to 14 carbon atoms. Most preferably, $R_4$ and $R_5$ are each independently of the other a substituted or unsubstituted alkyl of 1 to 10 carbon atoms, substituted or unsubstituted cylohexyl, substituted or unsubstituted phenyl, or phenylalkyl of 7 to 9 carbon atoms.

When E is —$COR_6COR_7$ or —$COR_8CONHR_9$, preferably, $R_6$ and $R_8$ are each independently of the other a substituted or unsubstituted alkylene of 1 to 8 carbon atoms and $R_7$ and $R_9$ are each independently of the other a substituted or unsubstituted alkyl of 1 to 8 carbon atoms, substituted or unsubstituted cycloalkyl of 5 to 8 carbon atoms, substituted or unsubstituted aryl of 6 to 12 carbon atoms or a substituted or unsubstituted phenylalkyl of 7 to 14 carbon atoms.

When E is —$COR_{10}$, preferably $R_{10}$ is a substituted or unsubstituted alkyl of 1 to 12 carbon atoms, substituted or unsubstituted cycloalkyl of 5 to 8 carbon atoms, substituted or unsubstituted phenyl, or substituted or unsubstituted phenylalkyl of 7 to 14 carbon atoms. Most preferably, E is a substituted or unsubstituted alkyl of 1 to 10 carbon atoms, substituted or unsubstituted cylohexyl, substituted or unsubstituted phenyl, or phenylalkyl of 7 to 9 carbon atoms.

When E is —$COOR_{11}$ or —$SO_2R_{12}$, preferably $R_{11}$ and $R_{12}$ are each independently of the other a substituted or unsubstituted alkyl of 1 to 8 carbon atoms, substituted or unsubstituted cycloalkyl of 5 to 8 carbon atoms, substituted or unsubstituted aryl of 6 to 12 carbon atoms or substituted or unsubstituted phenylalkyl of 7 to 14 carbon atoms.

The instant asymmetrical azo compounds are prepared in several steps. Depending on the desired end product, it is initially necessary to prepare one of two intermediates: an appropriate 1-substituted 4-amino, 4-alkylamino or 4-hydroxy-2,2,6,6-tetramethylpiperidine is converted into either the corresponding ester or amide derivative or the corresponding hydrazine ester or amide derivative. Conversion into the hindered amine ester or amide may be accomplished by reaction of the appropriate hindered amine with a halogenated ester such as methyl chloroformate. The resulting compound may then be converted into the corresponding hydrazine ester or amide derivative by reaction with hydrazine. Alternatively, to form the hydrazine ester or amide derivative, the 4-hydroxy, alkylamino or amino piperidine compound may be reacted with a carbamate compound such as ethyl carbamate.

In the next step, the above ester or amide piperidine derivative or the hydrazine ester or amide derivative is reacted with an appropriate coreactant to form the corresponding intermediate asymmetrical hydrazide, the choice of which coreactant depends upon the desired end product. These possibilities and the preparative methods therefor are illustrated below and are intended to be non-limitative in nature.

As a final step, the intermediate asymmetrical hydrazide compound is oxidized to prepare the instant asymmetrical azo compounds. The oxidizing agents which can be employed are fuming nitric acid, lead peroxide in cold dilute sulfufic acid, lead tetraacetate, t-butylhypochlorite, manganese dioxide, calcium hypochlorite, N-bromosuccinimide, nitrogen tetroxide and iodobenzene diacetate.

The intermediate asymmetrical HALS hydrazides are prepared by reacting (2,2,6,6-tetramethylperidinyl)esters with a primary or secondary alkyl hydrazine, hydrazine or hydrazine hydrate. The reaction is illustrated by the following equation.

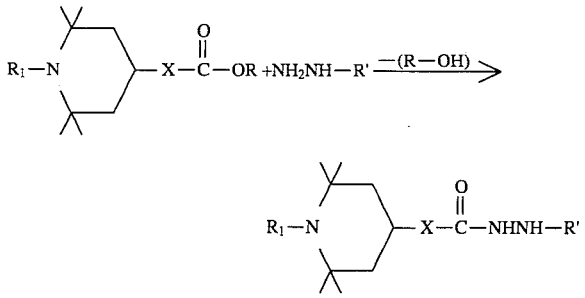

where $R_1$ and X are as previously defined, R is an alkyl of 1 to 20 carbons or phenyl and R' is a substituted or unsubstituted alkyl of 1 to 20 carbon atoms, substituted or unsubstituted cycloalkyl of 5 to 12 carbon atoms, substituted or unsubstituted aryl of 6 to 14 carbon atoms or phenylalkyl of 7 to 22 carbon atoms.

Typically the ester is dissolved in a polar solvent and converted to the desired hydrazide by stirring with an equivalent amount or slight excess of a primary or secondary alkylhydrazine, hydrazine or hydrazine hydrate. The reaction may go at room temperature or may require heating. Preferably the hydrazinolysis reaction is carded out in methanol or ethanol at 10°–30° C. but other solvents such as isopropanol or ethylene glycol are also acceptable. In most cases the resulting hydrazides can be purified by recrystallization from the lower alcohols.

The starting esters are known in the literature as described in U.S. Pat. Nos. 3,941,744, 3,975,462, 4,005,094, 4,241,208, 4,408,051, 4,526,966, 4,562,220, 4,689,416, 4,745,192, 4,755,602 and DE 3,523,679.

Examples of suitable hydrazines include hydrazine, hydrazine hydrate, 35–85% hydrazine hydrate, methylhydrazine, ethylhydrazine, propylhydrazine, isopropylhydrazine, n-butylhydrazine, sec-butylhydrazine, n-amylhydrazine, sec-amylhydrazine, n-hexylhydrazine and n-octylhydrazine and sec-octylhydrazine.

The carbamoyl and thiocarbamoyl derivatives are prepared by reacting the hydrazides with isocyanates or isothiocyanates in aprotic polar solvents such as tetrahydrofuran or dimethylformamide, as illustrated by the following equations.

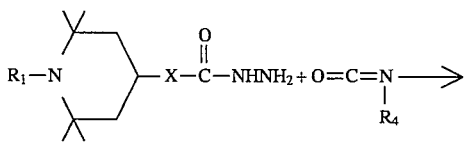

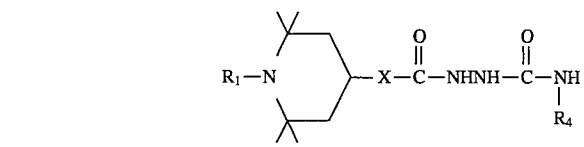

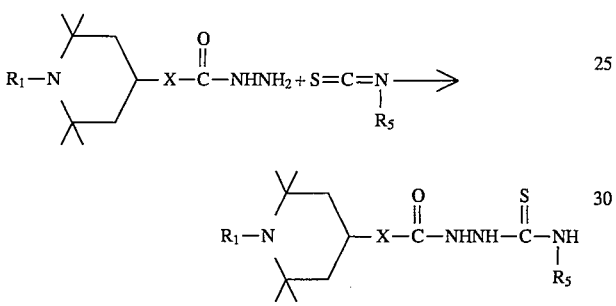

where $R_1$, $R_4$, $R_5$ and X are as previously defined.

The reactions of hydrazides isocyanates and isothiocyanates are well known in the art and can occur under a wide variety of temperatures, times, solvents and concentrations. Generally a mole ratio of 0.9 to 1.0 to 1.1 to 1.0 of the hydrazide to the monofunctional coreactant is employed.

The hydrazides also react with unsubstituted or N-substituted amic acid esters in lower alcohol solutions to form diacyl hydrazines.

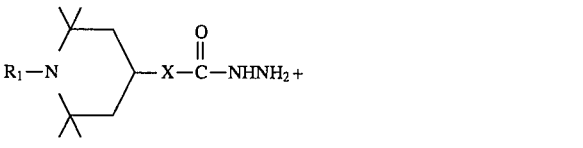

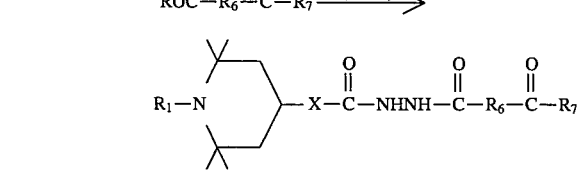

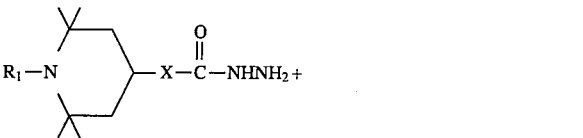

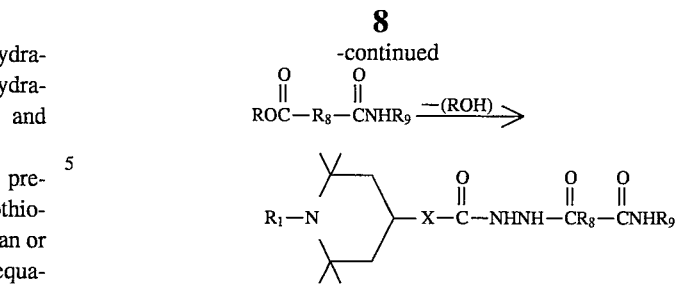

where $R_1$, $R_6$, $R_7$, $R_8$, $R_9$, R and X are as previously defined.

The reactions are normally carried out in refluxing alcohol (i.e. methanol) but may be carried out in higher boiling aprotic solvents or without solvent by heating a mixture of the two components above their melting points. The methyl and ethyl esters of N-substituted oxamates and succinamates are the preferred coreactants.

The acyl derivatives of the hydrazide may be prepared by reacting the esters (cited in the literature, as above) with acid hydrazides in refluxing alcohol (i.e. methanol).

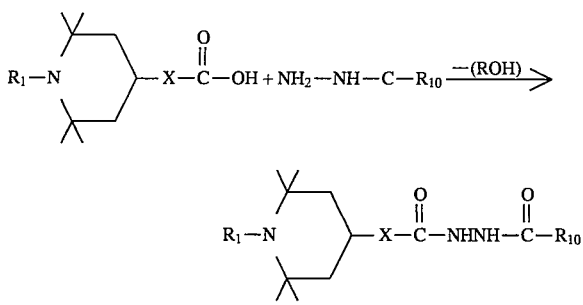

where $R_1$, $R_{10}$, R and X are as previously defined.

The acyl derivatives may also be prepared by reacting the hydrazides with non-cyclic carboxylic acid anhydrides:

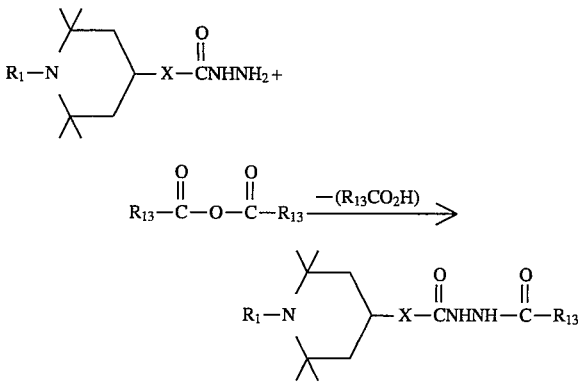

where $R_1$ and X are as defined above and $R_{13}$ is defined as $R_{10}$ above. The reactions are typically conducted in aprotic solvents, such as tetrahydrofuran, diethyl ether or t-butyl methyl ether. However, the reaction may also be carried out by adding the anhydride to a methanolic solution of the hydrazide. In addition, when $R_1$ is hydrogen, alkyl, allyl, benzyl or an alkyl substituted benzyl, the carboxylic acid generated in the reaction may form a salt with the hindered amine. The free base derivatives may be regenerated from the carboxylic acid salt by neutralizing the salt with a stronger base than the hindered amine, for example, dilute sodium hydroxide, dilute potassium hydroxide, hydrazine or more basic amines, such as diethylamine or triethylamine.

The alkoxycarbonyl, cycloalkoxycarbonyl, aryloxycarbonyl and aralkoxycarbonyl derivatives of the hydrazides may be prepared by reacting the ester, with the corresponding alkyl, cycloalkyl, aryl or aralkyl carbazates in refluxing alcohol (i.e. methanol).

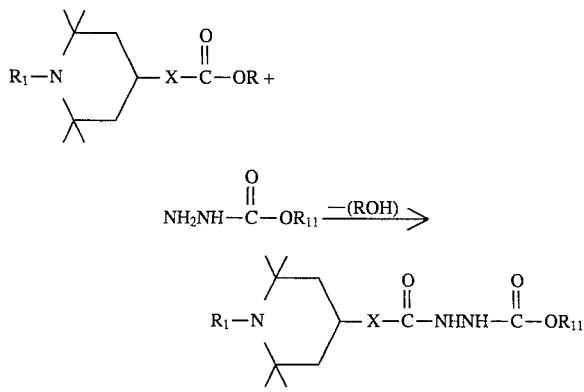

where $R_1$, $R_{11}$, R and X are as previously defined.

Alternatively, these derivatives may be prepared by reacting the hydrazide with a disubstituted carbonate or substituted haloformate. When a haloformate is used, an additional base may be used to react with the halogen acid formed. The amine group in the molecule may serve this purpose, but must then be released from its salt form by subsequent reaction with a strong base (as during workup).

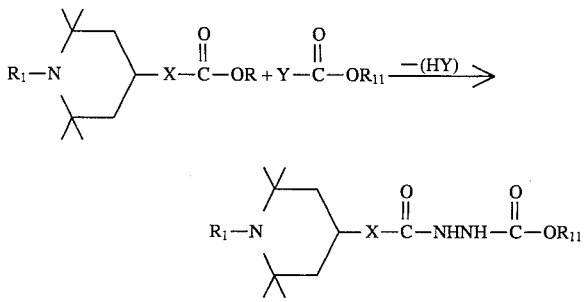

where $R_1$, $R_{11}$, R and X are as previously defined and Y is aryloxy or halogen.

The sulfonyl derivatives of the hydrazide may be prepared by reacting the esters of the literature with the corresponding sulfonyl hydrazide.

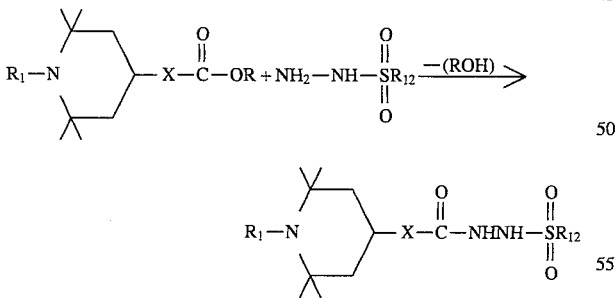

where $R_1$, $R_{12}$, R and X are as defined previously.

Examples of suitable isocyanates include allyl isocyanate, benzyl isocyanate, n-butyl isocyanate, sec-butyl isocyanate, isobutyl isocyanate, t-butyl isocyanate, cyclohexyl isocyanate, ethyl isocyanate, isopropyl isocyanate, 4-methoxyphenyl isocyanate, methyl isocyanate, octadecyl isocyanate, 1-naphthyl isocyanate, phenyl isocyanate, o-tolyl isocyanate, m-tolyl isocyanate and p-tolyl isocyanate, dimethyl-m-isopropenylbenzyl isocyanate and 2-isocyanatoethyl methacrylate.

Examples of suitable isothiocyanates include allyl isothiocyanate, benzyl isothiocyanate, 4-bromophenyl isothiocyanate, n-butyl isothiocyanate, sec-butyl isothiocyanate, isobutyl isothiocyanate, t-butyl isothiocyanate, 3-chlorophenyl isothiocyanate, cyclohexyl isothiocyanate, cyclohexyl isothiocyanate, ethyl isothiocyanate, methyl isothiopcyanate, propyl isothiocyanate, isopropyl isothiocyanate, 1-naphthyl isothiocyanate, t-octyl isothiocyanate, phenethyl isothiocyanate, phenyl isothiocyanate, propyl isothiocyanate, o-tolyl isothiocyanate, m-tolyl isothiocyanate and p-tolyl isothiocyanates.

Examples of suitable amic acid esters include methyl oxamate, ethyl oxamate, propyl oxamate, isopropyl oxamate, n-butyl oxamate, phenyl oxamate, methyl succinamates, ethyl succinamate, propyl succinamate, isopropyl succinamate, n-butyl succinamate, phenyl succinamate, ethyl N-(2,2,6,6-tetramethyl-4-piperidinyl)oxamate, methyl N-(2,2,6,6-tetramethyl-4-piperidinyl)oxamate, ethyl N-(2,2,6,6-tetramethyl-4-piperidinyl)succinamate, methyl N-(2,2,6,6-tetramethyl-4-piperidynyl)succinamate, ethyl N-(3,5-di-t-butyl-4-hydroxyphenyl)oxamate, methyl N-(3,5-di-t-butyl-4-hydroxyphenyl)oxamate, ethyl N-(3,5-di-t-butyl-4-hydroxyphenyl)succinamate and methyl N-(3,5-di-t-butyl-4-hydroxyphenyl)succinamate.

Examples of suitable acid hydrazides include acetyl hydrazide, propionic hydrazide, butyric hydrazide, isobutyric hydrazide, valetic hydrazide, isovaleric hydrazide, caproic hydrazide, decanoic hydrazide, lauric hydrazide, stearic hydrazide, benzhydrazide, 3,5-di-t-butyl-4-hydroxybenzhydrazide.

Examples of suitable carbazates include ethyl carbazate, methyl carbazate, propyl carbazate, isopropyl carbazate, butyl carbazate, cyclohexyl carbazate, cyclopentyl carbazate, cyclododecyl carbazate, phenyl carbazate, benzyl carbazate, 4-t-butylcyclohexyl carbazate, 2-ethylhexyl carbazate, 4-methylphenyl carbazate and 3-methoxyphenyl carbazate.

Examples of suitable sulfonyl halides include benzenesulfonyl hydrazide, 4-bromobenzenesulfonyl hydrazide, 1-butanesulfonyl hydrazide, 4-t-butylbenzenesulfonyl hydrazide, p-toluenesulfonyl hydrazide, ethanesulfonyl hydrazide, methanesulfonyl hydrazide, 4-fluorobenzenesulfonyl hydrazide, 1-hexadecanadulfonyl hydrazide, isopropanesulfonyl hydrazide and 1-naphthalenesulfonyl hydrazide.

The instant invention also pertains to a stabilized polymer composition which comprises (a) a polymer, copolymer or polymer blend which contains in at least one polymer or polymer component significant ethylenic unsaturation, and (b) an effective stabilizing amount of an asymmetrical azo derivative grafted to said polymer or polymer component, said derivative having before grafting the structure of formula IV

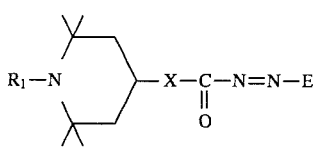

where $R_1$ is hydrogen, oxyl, hydroxyl, alkyl of 1 to 8 carbon atoms, alkyl of 2 to 4 carbon atoms substituted by one hydroxyl group, allyl, benzyl, benzyl substituted by one of two alkyl of 1 to 4 carbon atoms, alkoxy of 1 to 18 carbon atoms, cycloalkoxy of 5 to 12 carbon atoms or alkanoyl of 1 to 8 carbon atoms;

X is —O— or —NR₂— where R₂ is hydrogen, alkyl of 1 to 18 carbon atoms, cycloalkyl of 5 to 12 carbon atoms, phenylalkyl of 7 to 15 carbon atoms, alkyl of 2 to 4 carbon atoms substituted by one alkoxy group of 1 to 12 carbon atoms or a group of formula II

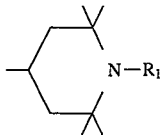

in which R₁ is as defined above; and

E is a substituted or unsubstituted alkyl of 1 to 20 carbon atoms, substituted or unsubstituted cycloalkyl of 5 to 12 carbon atoms, substituted or unsubstituted aryl of 6 to 14 carbon atoms or phenylalkyl of 7 to 22 carbon atoms, or E is —CONHR₄, —CSNHR₅, —COR₆COR₇, —COR₈CONHR₉, —COR₁₀, COOR₁₁ or —SO₂R₁₂, in which R₄, R₅, R₇, R₉, R₁₀, R₁₁ and R₁₂ are each independently of the other hydrogen, substituted or unsubstituted alkyl of 1 to 20 carbon atoms, substituted or unsubstituted cycloalkyl of 5 to 12 carbon atoms, substituted or unsubstituted aryl of 6 to 14 carbon atoms or phenylalkyl of 7 to 22 carbon atoms; and R₆ and R₈ are each independently of the other a substituted or unsubstituted alkylene of 1 to 12 carbons.

Further, the instant invention relates to the intermediate hydrazine derivatives of formula V

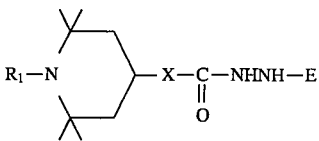

where

R₁ is an unsubstituted or substituted alkoxy of 1 to 18 carbon atoms or cycloalkoxy of 5 to 12 carbon atoms;

X is —O— or —NR₂— where R₂ is hydrogen, alkyl of 1 to 18 carbon atoms, cycloalkyl of 5 to 12 carbon atoms, phenylalkyl of 7 to 15 carbon atoms, alkyl of 2 to 4 carbon atoms substituted by one alkoxy group of 1 to 12 carbon atoms or a group of formula II

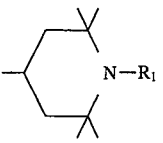

in which R₁ is as defined above; and

E is a substituted or unsubstituted alkyl of 1 to 20 carbon atoms, substituted or unsubstituted cycloalkyl of 5 to 12 carbon atoms, substituted or unsubstituted aryl of 6 to 14 carbon atoms or phenylalkyl of 7 to 22 carbon atoms, or E is —CONHR₄, —CSNHR₅, —COR₆COR₇, —COR₈CONHR₉, —COR₁₀, —COOR₁₁ or —SO₂R₁₂, in which R₄, R₅, R₇, R₉, R₁₀, R₁₁ and R₁₂ are each independently of the other hydrogen, substituted or unsubstituted alkyl of 1 to 20 carbon atoms, substituted or unsubstituted cycloalkyl of 5 to 12 carbon atoms, substituted or unsubstituted aryl of 6 to 14 carbon atoms or phenylalkyl of 7 to 22 carbon atoms; and R₆ and R₈ are each independently of the other a substituted or unsubstituted alkylene of 1 to 12 carbons.

Some compounds of the general formula (V) are described in EP 0,467,344 A1, where the N-atom of the piperdine moiety is substituted by groups other than alkoxy or cycloalkoxy.

The polymers, copolymers or polymer blends having significant ethylenic unsaturation in at least one polymer or polymer component, useful as component (a) in the stabilized compositions, are selected from the group consisting of ABS, HIPS, emulsion SBR, PP/EPDM, PP/NBR, PP/NR, ABS/PC, ABS/nylon, ABS/PVC, ABS/polyester, ABS/SMA, ABS/polysulfone, ASA/PC, acetal/elastomer, polyester/elastomer, nylon/elastomer, PPO/NR, EPDM/NBR and EPDM/olefin.

Preferably component (a) is ABS or ABS/PC.

When any of R₁ or R₂ is alkyl, such alkyl groups are, for example, methyl, ethyl, isopropyl, n-butyl, isobutyl, tert-butyl, tert-amyl, 2-ethylhexyl, n-octyl, tert-octyl, lauryl, tert-dodecyl and octdecyl; when such radicals are cycloalkyl, they are, for example, cyclopentyl, cyclohexyl, cyclooctyl and cyclododecyl; when said radicals are phenylalkyl, they are, for example benzyl, phenethyl, α-methylbenzyl and α,α-dimethylbenzyl; when said radicals are alkoxy, they are, for example, methoxy, ethoxy, octyloxy and dodecyloxy; when said radicals are cycloalkoxy, they are, for example, cyclohexyloxy and cyclooctyloxy; and, when said radicals are alkanoyl, they are, for example, acetyl, propionyl, butanoyl and octanoyl.

In general polymers which can be stabilized include
1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.
2. Mixtures of the polymers mentioned under 1), for example mixtures of polypropylene with polyisobutylene.
3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.
4. Polystyrene, poly-(p-methylstyrene).
5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.
6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.
8. Polymers which are derived from α,β-unsaturated acids and derivatives thereof, such as polyacrylates and polymethacrylates, polyacrylamide and polyacrylonitrile.
9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.
10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.
11. Homopolymers and copolymers of cyclic ethers, such as polyalkylene glycols, polyethylene oxide, polypropylene oxide or copolymers thereof with bis-glycidyl ethers.
12. Polyacetals, such as polyoxymethylene and those polyoxymethylenes which contain ethylene oxide as comonomer.
13. Polyphenylene oxides and sulfides, and mixtures of polyphenylene oxides with polystyrene.
14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).
15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalate, poly-p-phenylene terephthalamide or poly-m-phenylene isophthalamide, as well as copolymers thereof with polyethers, such as for instance with polyethylene glycol, polypropylene glycol or polytetramethylene glycols.
16. Polyureas, polyimides and polyamide-imides.
17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane]terephthalate and polyhydroxybenzoates as well as block-copolyether-esters derived from polyethers having hydroxyl end groups.
18. Polycarbonates.
19. Polysulfones, polyethersulfones and polyetherketones.
20. Crosslinked polymers which are derived from aldehydes on the one hand and phenols, ureas and melamines on the other hand, such as phenol/formaldehyde resins, urea/formaldehyde resins and melamine/formaldehyde resins.
21. Drying and non-drying alkyd resins.
22. Unsaturated polyester resins which am derived from copolyesters of saturated and unsaturated dicarboxylic acids with polyhydric alcohols and vinyl compounds as crosslinking agents, and also halogen-containing modifications thereof of low flammability.
23. Thermosetting acrylic resins, derived from substituted acrylic esters, such as epoxy-acrylates, urethane-acrylates or polyester acrylates.
24. Alkyd resins, polyester resins or acrylate resins in admixture with melamine resins, urea resins, polyisocyanates or epoxide resins as crosslinking agents.
25. Crosslinked epoxide resins which are derived from polyepoxides, for example from bis-glycidyl ethers or from cycloaliphatic diepoxides.
26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.
27. Mixtures of polymers as mentioned above, for example PP/EPDM, Polyamide 6/EPDM or ABS, PVC/EVA, PVC/ABS, PVC/MBS, PC/ABS, PBTP/ABS.
28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.
29. Aqueous emulsions of natural or synthetic rubber, e.g. natural latex or latices of carboxylated styrene/butadiene copolymers.
30. Polysiloxanes such as the soft, hydrophilic polysiloxanes described, for example, in U.S. Pat. No. 4,259,467; and the hard polyorganosiloxanes described, for example, in U.S. Pat. No. 4,355,147.
31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
32. Radiation curable compositions containing ethylenically unsaturated monomers or oligomers and a polyunsaturated aliphatic oligomer.
33. Epoxymelamine resins such as light-stable epoxy resins crosslinked by an epoxy functional coetherified high solids melamine resin such as LSE-4103 (Monsanto).

In general, the compounds of the present invention axe employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants
    1.1. Alkylated 2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated hydroquinones, for example, 2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers, for example, 2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for example, 2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl]terephthalate.

1.5. Benzyl compounds, for example, 1,3,5-tri-(3,5-di-tert-butyl-4-hydroxybenzyl)-2,4,6-trimethylbenzene
di-(3,5-di-tert-butyl-4-hydroxybenzyl)sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl)isocyanurate
1,3,5-tris-(4-tert-butyl-3-hydroxy-2,6-dimethylbenzyl)isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example, 4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example, methanol
octadecanol
1,6-hexanediol
neopentyl glycol
thiodiethylene glycol
diethylene glycol
triethylene glycol
pentaerythritol
tris-hydroxyethyl isocyanurate
di-hydroxyethyl oxalic acid diamide 1.8. Esters of β-(5-tert-butyl-4-hydroxy-3-methylphenyl)-propionic acid with monohydric or polyhydric alcohols, for example, methanol
octadecanol
1,6-hexanediol
neopentyl glycol
thiodiethylene glycol
diethylene glycol
triethylene glycol
pentaerythritol
tris-hydroxyethyl isocyanurate
di-hydroxyethyl oxalic acid diamide 1.9. Amides of β-(3,5-di-tertrbutyl-4-hydroxyphenyl)-propionic acid for example, N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 1.10 Diarylamines, for example, diphenylamine, N-phenyl-1-naphthylamine, N-(4-tert-octylphenyl)-1-naphthylamine,
4,4'-di-tert-octyl-diphenylamine, reaction product of N-phenylbenzylamine and
2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers 2.1. 2-(2'-Hydroxyphenyl)-benzotriazoles, for example, the 5'-methyl-,
3',5'-di-tert-butyl-, 5'-tert-butyl-, 5'-(1,1,3,3-tetramethylbutyl)-,
5-chloro-3',5'-di-tert-butyl-, 5-chloro-3'-tert-butyl-5'-methyl-, 3'-sec-butyl-5'-tert-butyl-,
4'-octoxy, 3',5'-di-tert-amyl-, 3',5'-bis-(α,α-dimethylbenzyl),
3'-tert-butyl-5'-(2-(omega-hydroxy-octa-(ethyleneoxy)carbonyl-ethyl)-,
3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl)sebacate, bis-(1,2,2,6,6-pentamethylpiperidyl)sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5 -tetramethylpiperazinone), bis(1-octyloxy-2,2,6,6-tetramethylpiperidin-4-yl)sebacate.

2.7. Oxalic acid diamides, for example, 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4 -(2-hydroxyethoxy)phenyl]-6-(4-chlorophenyl)-s-triazine; 2,4-bis[2-hydroxy-4-(2 -hydroxy-4-(2-hydroxyethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4 -hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyldithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nittone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3, 5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4 -tert-butyl-3-hydroxybenzyl)isocyanurate, 1,1,3,-tris(2-methyl-4-hydroxy-5-tert-butylphenyl)butane, 1,3,5-tris[2 -(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5 -di-tert-butyl-4-hydroxyanilino)-3,5-di(octylthio)-s-triazine, N,N'-hexamethylene-bis(3,5 -di-tert-butyl-4-hydroxyhydrocinnamamide), calcium bis(ethyl 3,5-di-tert-butyl-4 -hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis [2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5 -di-tert-butyl-4-hydroxybenzyl) isocyanurate, 2,6-di-tert-butyl-p-cresol or 2,2'-ethylidene-bis-(4,6-di-tert-butylphenol).

The hindered amine compound of particular interest is selected from the group consisting of bis(2,2,6,6-tetramethylpiperidin-4-yl)sebacate, bis(1,2,2,6,6-pentamethylpiperidin-4-yl)sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl)nitrilotriacetate, 1,2-bis(2,2,6,6-tetramethyl-3-oxopiperazin-4-yl)ethane, 2,2,4,4-tetramethyl-7-oxa-3,20 -diaza-21-oxodispiro[5.1.11.2] heneicosane, polycondensation product of 2,4-dichloro-6 -tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6 -bis(butyl-2,2,6,6-tetramethyl-piperidin-4-yl)-amino-s-triazin-2-yl]-1,10-diamino-4,7-diaza decane, mixed [2,2,6,6-tetramethylpiperidin-4-yl/β,β,β',β'-tetramethyl-3,9-(2,4,8,10 -tetraoxaspiro[5.5]-undecane)diethyl]1, 2,3,4-butanetetracarboxylate, mixed [1,2,2,6,6-pentamethyl piperidin-4-yl/β,β,β',β'-tetramethyl-3,9-(2,4,8,10-tetraoxaspiro[5.5]undecane)diethyl]1,2,3,4-butanetetracarboxylate, octamethylene bis(2,2,6,6-tetramethyl-piperidin- 4-carboxylate), 4,4'-ethylenebis(2,2,6,6-tetramethylpiperazin-3-one), and bis(1-octyloxy-2,2,6,6-tetramethylpiperidin-4-yl)sebacate.

A most preferred hindered amine compound is bis(2,2,6,6-tetramethylpiperidin-4-yl) sebacate, the polycondensation product of 1-(2-hydroxyethyl)-2,2,6,6-tetramethyl-4 -hydroxypiperdine and succinic acid, the polycondensation product of 2,4-dichloro-6-tert-octylamino-s-triazine and 4,4'-hexamethylenebis(amino-2,2,6,6-tetramethylpiperidine), N,N',N'',N'''-tetrakis[(4,6-bis(butyl-(2,2,6,6-tetramethyl-piperidin-4-yl)amino)-s-triazine-2-yl]-1,10-diamino-4,7-diazadecane or bis(1-octyloxy-2,2,6,6-tetramethylpiperidin-4-yl)sebacate.

The following examples are presented for the purpose of illustration only and are not to be construed to limit the nature or scope of the instant invention in any manner whatsoever.

EXAMPLE 1

Bis(1-methoxy-2,2,6,6-tetramethylpiperidin-4-yl) Hydrazine-1,2-dicarboxylate

To a mixture of 15.8 g of 1-methoxy-2,2,6,6-tetramethylpipefidin-4-ol and 5.9 g of dimethyl hydrazine-1,2-dicarboxylate is added 1.4 g of tetrabutyl titanate at room temperature. The mixture is heated at 135°–145° C. for 12 hours and methanol is collected in a Dean-Stark trap. The reaction mixture is partitioned between toluene and water. The organic phase is then washed with water, brine, dried over anhydrous sodium sulfate and evaporated to leave 19.1 g of the crude desired product. Recrystallization of the crude product from acetonitrile affords 11.7 g of the title compound as an off-white solid; mp 147°–149° C.

Analysis: Calcd. for $C_{22}H_{42}N_4O_6$: C, 57.6; H, 9.2.; N, 12.2. Found: C, 57.6; H, 9.4, N, 12.1.

EXAMPLE 2

Bis(1-cyclohexyloxy-2,2,6,6-tetramethylpiperidin-4-yl) Hydrazine-1,2-dicarboxylate The procedure of Example 1 is repeated using 24.1 g of 1-cyclohexyloxy-2,2,6,6 -tetramethylpiperidin-4-ol, 6.67 g of dimethyl hydrazine-1,2-dicarboxylate and 1.5 g of tetrabutyl titanate to afford 14.6 g of the title compound as a white solid; mp 150°–152° C.

Analysis: Calcd. for $C_{32}H_{58}N_4O_6$: C, 64.4; H, 10.1; N, 9.4. Found: C, 64.4; H, 10.2; N, 9.3.

EXAMPLE 3

Bis(1,2,2,6,6-pentamethylpiperidin-4-yl) Hydrazine-1,2-dicarboxylate

The procedure of Example 1 is repeated using 33.9 g of 1,2,2,6,6 -pentamethylpiperidin-4-ol, 13.3 g of dimethyl hydrazine-1,2-dicarboxylate and 0.31 g of tetrabutyl titanate to afford 14.8 g of the title compound as a white solid; mp 189°–191° C.

Analysis: Calcd. for $C_{22}H_{42}N_4O_4$: C, 61.9; H, 9.9; N. 13.1. Found: C, 61.8; H, 10.2,; N, 13.0.

EXAMPLE 4

Bis(1-methoxy-2,2,6,6-tetramethylpiperidin-4-yl) Azodicarboxylate

To a solution of 8.2 g of bis(1-methoxy-2,2,6,6-tetramethylpiperidin-4-yl) hydrazine-1,2-dicarboxylate, as prepared in Example 1, in 100 mL of methylene chloride is added 6.3 g of iodobenzene diacetate in one portion at room temperature. After stirring at room temperature for 50 minutes, the solution is washed with a 10% solution of sodium carbonate and then with brine, and dried over anhydrous magnesium sulfate. The dried solution is then evaporated to leave 9.3 g of the desired product. Recrystallization of the crude product from acetonitrile affords 6.5 g of the title compound; mp 145°–147° C.

Analysis: Calcd. for $C_{22}H_{40}N_4O_6$: C, 57.8; H, 8.8; N, 12.3. Found: C, 57.3; H, 9.2; N, 11.9.

EXAMPLE 5

Bis(1-octyloxy-2,2,6,6-tetramethylpiperidin-4-yl) Hydrazine-1,2-dicarboxylate

To a solution of 29.7 g of triphosgene in 120 mL of tetrahydrofuran (THF) is added a solution of 85.7 g of 1-octyloxy-2,2,6,6-tetramethylpiperidin-4-ol and 42.0 mL of triethylamine in 240 mL of THF over 4 hours at 5°–10° C., followed by 7.3 mL of hydrazine hydrate. After stirring the reaction mixture at room temperature for 18 hours, a solution of 71.0 g of sodium carbonate in 500 mL of water is added and the organic layer is removed, washed with water and dried over anhydrous magnesium sulfate. The dried solution is evaporated to afford 97.2 g of the title compound as an oil.

NMR and mass spectra are consistent with the desired structure of the title compound.

EXAMPLE 6

Bis(1,2,2,6,6-pentamethylpiperidin-4-yl)
Hydrazine-1,2-dicarboxylate

The procedure of Example 5 is repeated using 178.2 g of triphosgene, 308.4 g of 1,2,2,6,6-pentamethylpiperidin-4-ol, 252 mL of triethylamine and 43.7 mL of hydrazine hydate to afford 180 g of the title compound as a white solid; mp 189°–191° C.

EXAMPLE 7

Bis(1,2,2,6,6-pentamethylpiperidin-4-yl)
Azodicarboxylate

To a solution of 30.0 g bis(1,2,2,6,6-pentamethylpiperidin-4-yl) hydrazine-1,2 -dicarboxylate in 60 mL of methylene chloride is added 16.0 g (10.8 mL), of trifluoroacetic acid at 0°–5° C., followed the addition of 22.6 g of iodobenzene diacetate at room temperature. After stirring at room temperature for 2.5 hours, the reaction mixture is washed with saturated sodium bicarbonate solution and then with brine, and dried over anhydrous magnesium sulfate. The dried solution is evaporated to afford a pale yellow oil. Trituration with acetonitrile affords 7.0 g of the title compound as a pale yellow solid; mp 135°–137° C. NMR and IR analyses are consistent with the desired structure.

Analysis: Calcd. for $C_{22}H_{40}N_4O_4$: C, 62.2; H, 9.5; N, 13.2 Found: C, 61.9; H, 10.0; N, 12.8.

EXAMPLE 8

Bis(1-octyloxy-2,2,6,6-tetramethylpiperidin-4-yl)
Azodicarboxylate

The procedure of Example 4 is repeated using 4.6 g of bis(1-octyloxy-2,2,6,6 -tetramethylpiperidin-4-yl) hydrazine-1,2-dicarboxylate and 2.3 g of iodobenzene diacetate to afford 3.3 gg of the title compound as a pale yellow oil. NMR, IR and mass spectra analyses are consistent with the desired structure.

EXAMPLE 9

Bis(1-cyclohexyloxy-2,2,6,6-tetramethylpiperidin-4-yl)
Azodicarboxylate

The procedure of Example 4 is repeated using 12.2 g of bis(1-cyclohexyloxy-2,2,6,6-tetramethylpiperidin-4-yl) hydrazine-1,2-dicarboxylate and 7.2 g of iodobenzene diacetate to afford 10.3 g of the title compound; mp 189°–19 1° C.

Analysis: Calcd. for $C_{32}H_{56}N_4O_6$: C, 64.6; H, 9.8; N, 9.4. Found: C, 64.6; H, 9.7; N, 9.4.

EXAMPLE 10

Grafting of Stabilizers to ABS Resin

ABS resin (342 EZ, Dow) is solvent-blended with 0.5% by weight of a test light stabilizer and then the blended ABS resin is extruded at zone temperatures in the range of 390°–425° F. (199°–218° C.) at an extruder speed set at 25 or 100 rpm. The lower 25 rpm affords a longer residence time for the resin in the extruder. The resulting pellets are divided into two portions to study the light stability of solvent extracted and non-extracted ABS samples.

The extruded ABS resin is dry blended with titanium dioxide and then milled and compression molded at 365° F. (185° C.) into 4"×4" (10.16 cm×10.16 cm) plaques and cut into 1" (2.54 cm) specimens. A portion of the extruded ABS resin is dissolved in xylene and the polymer precipitated by the addition of methanol. The polymer crumbs are dried and then solvent blended with 0.1% by weight of n-octadecyl 3,5-di-tert-butyl-4-hydroxyhydrocinnamate and 1% by weight of titanium dioxide, followed by milling and compression molding as outlined above. Both samples (extracted and non-extracted) are exposed in standard interior automotive Xenon Arc WeatherOmeter (XAW) and ACS tests. ΔE color measurements are made at 50 hour intervals. The amount of light stabilizer that is grafted onto the polymer is also determined by liquid chromatography (LC).

TABLE A

Non-Extracted Grafted ABS Resin

| Stabilizer* | Conc. % by wt | ΔE Values** after Hours of Exposure (Interior Automotive Xenon) | | | | |
|---|---|---|---|---|---|---|
| | | 50 | 100 | 150 | 200 | 275 |
| Base | — | 1.5 | 4.4 | 7.3 | 10.1 | 13.8 |
| HALS A | 0.5 | 1.1 | 0.5 | 0.8 | 1.5 | 3.3 |
| Compound of Example 4 | 0.5 | 0.8 | 1.7 | 4.3 | 6.3 | 9.1 |

*HALS A is bis(1,2,2,6,6-pentamethylpiperidin-4-yl) sebacate.
**Lower numbers indicate better color performance.

TABLE B

Extracted Grafted ABS Resin

| Stabilizer* | Conc. % by wt | ΔE Values** after Hours of Exposure (Interior Automotive Xenon) | | | | |
|---|---|---|---|---|---|---|
| | | 50 | 100 | 150 | 200 | 275 |
| Base | — | 1.5 | 4.4 | 7.3 | 10.1 | 17.4 |
| HALS A | 0.5 | 1.4 | 4.5 | 7.6 | 11.9 | 15.3 |
| Compound of Example 4 | 0.5 | 0.8 | 1.7 | 4.3 | 6.3 | 7.6 |

*HALS A is bis(1,2,2,6,6-pentamethylpiperidin-4-yl) sebacate.
**Lower numbers indicate better color performance.

The above data in Tables A and B illustrate the light stabilizing activity of the instant compound of Example 4, which activity is maintained even after the ABS resin is extracted in xylene as compared to HALS A, a non-graftable control light stabilizer which is removed from the ABS resin by extraction.

Analytical data indicating the chemical bonding of the compound of Example 4 to the polymer substrate during the reactive extrusion processing are summarized in Table C. These data are the results of two replicate samples analyzed by liquid chromatography on the xylene solution obtained after the ABS resin has been extracted.

TABLE C

| Stabilizer* | Initial Conc. (% by wt) Before Extraction | Concentration (% by wt) After Extraction | Percent Extract. of Init. Conc. |
|---|---|---|---|
| HALS A | 0.5 | 0.1 | 80 |
| Compound of Example 4 | 0.5 | 0.5 | 0 |

*HALS A is bis(1,2,2,6,6-pentamethylpiperidin-4-yl) sebacate.

These data show that a vast portion of the prior art hindered amine light stabilizer is extracted when the extruded ABS resin is extracted with xylene solvent, but that the instant compounds as typified by the compound of Example 4 are chemically bonded to the ABS resin substrate and are not removed by solvent extraction.

EXAMPLE 11

Grafting of Stabilizers to ABS Resin

A representative example of the instant light stabilizers is incorporated into polybutadiene rubber (DIENE 55, Firestone Tire and Rubber Co.) using a Brabender Plasticorder, at 100° C. under nitrogen for seven minutes. Any non-grafted light stabilizer is removed from the polybutadiene by dissolving the polymer in xylene, followed by precipitation by the addition of methanol. The resulting polymer is dried (40° C., air oven). The total nitrogen analysis of the polymer samples before and after extraction indicates the substantial grafting of the instant compound to polybutadiene rubber during the processing step.

TABLE D

| Stabilizer* | Initial Conc. (% by wt) Before Extraction | Concentration (% by wt) After Extraction | Percent Extract. of Init. Conc. |
|---|---|---|---|
| Compound of Example 9 | 2.0 | 1.51 | 25 |

These data show that, when polybutadiene rubber is extracted with xylene solvent, the instant compounds as typified by the compound of Example 9 are chemically bonded to the polybutadiene substrate and are not prone to be removed by solvent extraction in a substantial fashion.

EXAMPLE 12

Light Stabilization of ABS/Polycarbonate Blends

A 50/50 blend of ABS (containing a hindered amine stabilizer compound) and polycarbonate is prepared by compounding the mixed resin pellets in a mini Brabender extruder. Injection molded 125 mil (3.2 mm) Izod bars are then prepared for evaluation of light stability, under interior automotive Xenon Arc WeatherOmeter exposure and spray Xenon Arc WeatherOmeter exposure test as described in Example 10. The results are given in Tables E and F below.

TABLE E

Light Stability Performance during GM-XAW Exposure

| Stabilizer* | Conc. % by wt | ΔE Values** after Hours of Exposure | | | |
|---|---|---|---|---|---|
| | | 102 | 200 | 400 | 600 |
| Base | — | 9.7 | 17.1 | 26.1 | 26.9 |
| HALS A | 0.5 | 9.1 | 15.7 | 23.5 | 24.2 |
| HALS B | 0.5 | 8.5 | 14.4 | 22.9 | 23.0 |
| Compound of Example 7 | 0.5 | 6.8 | 12.8 | 20.3 | 20.5 |
| Compound of Example 4 | 0.5 | 5.8 | 11.8 | 19.4 | 20.8 |

*HALS A is bis(1,2,2,6,6-pentamethylpiperidin-4-yl) sebacate. HALS B is bis(2,2,6,6-tetramethylpiperidin-4-yl) sebacate.
**Lower numbers indicate better color performance.

TABLE F

Light Stability Performance during XAW with Spray Exposure

| Stabilizer* | Conc. % by wt | ΔE Values** after Hours of Exposure | | | | |
|---|---|---|---|---|---|---|
| | | 230 | 406 | 600 | 800 | 1213 |
| Base | — | 1.2 | 5.9 | 11.2 | 15.0 | 21.1 |
| HALS A | 0.5 | 0.6 | 3.2 | 6.4 | 9.4 | 15.5 |
| HALS B | 0.5 | 1.1 | 1.8 | 5.0 | 8.3 | 14.4 |
| Compound of Example 7 | 0.5 | 1.3 | 0.9 | 4.4 | 7.3 | 12.8 |
| Compound of Example 4 | 0.5 | 1.0 | 1.3 | 3.4 | 6.6 | 12.6 |

*HALS A is bis(1,2,2,6,6-pentamethylpiperidin-4-yl) sebacate. HALS B is bis(2,2,6,6-tetramethylpiperidin-4-yl) sebacate.
**Lower numbers indicate better color performance.

The above data clearly demonstrate the advantages of the instant invention. When a hindered amine light stabilizer is located into the ABS phase of a ABS/polycarbonate blend, thus preventing its migration into the polycarbonate, the overall light stability of the blend is improved.

EXAMPLES 13–19

Following the general procedure of Example 1 or Example 5, the following compounds of formula III are prepared.

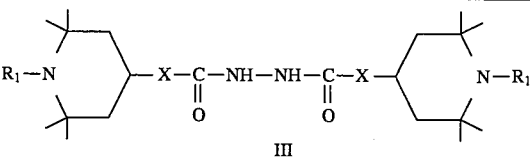

III

| Example | $R_1$ | X |
|---|---|---|
| 13 | methoxy | —NH— |
| 14 | cyclohexyloxy | —NH— |
| 15 | methyl | —NH— |
| 16 | octyloxy | —NH— |
| 17 | 2-hydroxyethyl | —O— |

-continued

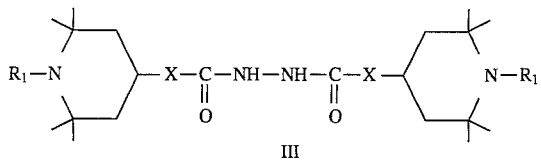
III

| Example | R₁ | X |
|---|---|---|
| 18 | benzyl | —O— |
| 19 | hydrogen | —O— |

EXAMPLES 20–26

Following the general procedure of Example 4 or Example 7, the compounds of formula I are prepared.

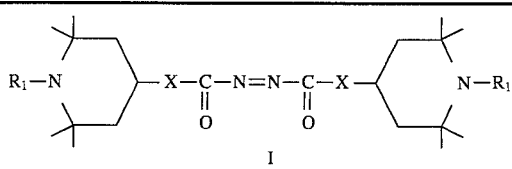
I

| Example | R₁ | X |
|---|---|---|
| 20 | methoxy | —NH— |
| 21 | cyclohexyloxy | —NH— |
| 22 | methyl | —NH— |
| 23 | octyloxy | —NH— |
| 24 | 2-hydroxyethyl | —O— |
| 25 | benzyl | —O— |
| 26 | hydrogen | —O— |

EXAMPLE 27

1-Methoxy-2,2,6,6-tetramethylpiperidin-4-yl Cloroformate

The title compound is prepared by reacting 1-methoxy-2,2,6,6-tetramethylpiperidin-4-ol (1 mole) with methylchloroformate (1 mole).

EXAMPLE 28

1-Methoxy-2,2,6,6-tetramethylpiperidin-4-yl Carbazate

The title compound is prepared by reacting the compound of Example 27 (1 mole) with hydrazine (1.1 mole), employing methanol as the solvent.

EXAMPLE 29

1-Methoxy-2,2,6,6-tetramethylpipefidin-4-yl 2-Methylhydrazinecarboxylate

The title compound is prepared by reacting the compound of Example 27 (1 mole) with methylhydrazine (1.1 mole) in methanol.

EXAMPLE 30

1-Methoxy-2,2,6,6-tetramethylpiperidin-4-yl 2-Isobutylcarbamoylhydrazinecarboxylate To obtain the title compound, the compound of Example 28 (1 mole) is reacted with isobutyl isocyanate (1.1 mole) in tetrahydrofuran.

EXAMPLE 31

1-Methoxy-2,2,6,6-tetramethylpiperidin-4-yl 2-Allylthiocarbamoylhydrazinecarboxylate To obtain the title compound, the compound of Example 28 (1 mole) is reacted with allyl isothiocyanate (1.1 mole), employing dimethylformamide as the solvent.

EXAMPLE 32

1-Methoxy-2,2,6,6-tetramethylpiperidin-4-yl 2-Succinamoylhydrazinecarboxylate

The title compound is prepared by reacting the compound of Example 28 (1 mole) with isopropyl succinamate (1 mole), employing methanol as the solvent.

EXAMPLE 33

1-Methoxy-2,2,6,6-tetramethylpiperidin-4-yl N-(3,5-Di-tert-butyl-4-hydroxyphenyl) succinamoylhydrazinecarboxylate The title compound is made by the reaction of the compound of Example 28 with ethyl N-(3,5-di-tert-butyl-4-hydroxyphenyl)succinamate in methanol.

EXAMPLE 34

1-Methoxy-2,2,6,6-tetramethylpiperidin-4-yl) 2-Acetylhydrazinecarboxylate

The title compound is prepared by reacting the compound of Example 27 (1 mole) with acetyl hydrazide (1 mole) in methanol.

EXAMPLE 35

1-Methoxy-2,2,6,6-tetramethylpiperidin-4-yl 2-Hydrazinocarbonylhydrazinecarboxylate The title compound is prepared by reacting the compound of Example 28 (1 mole) with methyl carbazate (1 mole) by refluxing the reaction mixture in methanol.

EXAMPLE 36

1-Methoxy-2,2,6,6-tetramethylpiperidin-4-yl 2-Benzenesulfonylhydrazinecarboxylate The title compound is prepared by reacting the compound of Example 27 (1 mole) with benzenesulfonyl hydrazide (1 mole).

EXAMPLE 37

The procedure of Example 4 is repeated using the asymmetrical hydrazide compounds of Examples 29–36, respectively, to obtain the following corresponding asymmetrical azo compounds of formula IVa:

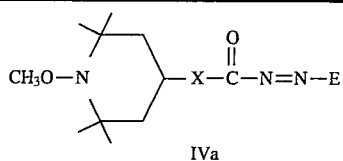

| Example | Hydrazide Compound | Azo Compound |
|---|---|---|
| A | 29 | methyl |
| B | 30 | —CONH-isobutyl |
| C | 31 | —CSNH-allyl |
| D | 32 | —COCH$_2$CH$_2$CONH$_2$ |
| E | 33 | —COCH$_2$CH$_2$CHNH—(3,5-di-t-Bu-4-OH-phenyl) |
| F | 34 | acetyl |
| G | 35 | —CONHNH$_2$ |
| H | 36 | —SO$_2$-phenyl |

EXAMPLE 38

Grafting of Stabilizers to ABS Resin

The procedure of Example 11 is repeated using the instant asymmetrical azo compounds of Example 37 A–H, respectively.

The instant compounds are chemically bonded to the polybutadiene substrate and are not prone to be removed by solvent extraction to any substantial degree.

EXAMPLE 39

Light Stabilization of ABS/Polycarbonate Blends

The procedure of Example 12 is repeated using the instant asymmetrical azo compounds of Examples 37 A–H, respectively.

The instant compounds, located into the ABS phase of an ABS/polycarbonate blend improve the overall light stability of the polymer blend.

EXAMPLES 40–42

Following the general procedure of Example 29, the following compounds of formula V are prepared.

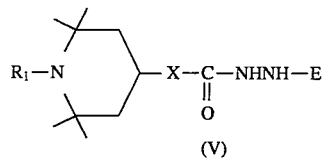

| Example | R$_1$ | X | E |
|---|---|---|---|
| 40 | methoxy | —NH— | ethyl |
| 41 | cyclohexyloxy | —NH— | propyl |
| 42 | octyloxy | —O— | n-amyl |

EXAMPLES 43–44

Using the general procedure of Example 30, the following instant compounds of formula V are prepared.

| Example | R$_1$ | X | E |
|---|---|---|---|
| 43 | methoxy | —NH— | —CONH-benzyl |
| 44 | ethoxy | —O— | —CONH-octadecyl |

EXAMPLES 45–47

Using the general procedure of Example 31, the following instant compounds of formula V are prepared.

| Example | R$_1$ | X | E |
|---|---|---|---|
| 45 | methoxy | —NH— | —CSNH-n-butyl |
| 46 | cyclohexyloxy | —NH— | —CSNH-(3-chlorophenyl) |
| 47 | octyloxy | —O— | —CSNH-cyclohexyl |

EXAMPLES 48–49

Using the general procedure of Example 32, the following instant compounds of formula V are prepared.

| Example | R$_1$ | X | E |
|---|---|---|---|
| 48 | methoxy | —NH— | -succinamoyl |
| 49 | octyloxy | —O— | -succinamoyl |

EXAMPLES 50–51

Using the general procedure of Example 33, the following instant compounds of formula V are prepared.

| Example | R$_1$ | X | E |
|---|---|---|---|
| 50 | ethoxy | —NH— | N-(3,5-di-tert-butyl-4-hydroxyphenyl)succinamoyl |
| 51 | benzyloxy | —O— | N-(3,5-di-tert-butyl-4-hydroxyphenyl)succinamoyl |

EXAMPLES 52–53

Using the general procedure of Example 34, the following instant compounds of formula V are prepared.

| Example | R$_1$ | X | E |
|---|---|---|---|
| 52 | propyloxy | —NH— | —COC$_2$H$_5$ |
| 53 | cyclohexyloxy | —O— | —COC$_3$H$_7$ |

EXAMPLES 54–55

Using the general procedure of Example 35, the following instant compounds of formula V are prepared.

| Example | R₁ | X | E |
|---|---|---|---|
| 54 | benzyloxy | —NH— | —COOC₂H₅ |
| 55 | octyloxy | —O— | —COOC₃H₇ |

EXAMPLES 56–57

Using the general procedure of Example 36, the following instant compounds of formula V are prepared.

| Example | R₁ | X | E |
|---|---|---|---|
| 66 | methoxy | —NH— | 4-bromobenzenesulfonyl |
| 67 | benzyloxy | —O— | 1-butanesulfonyl |

EXAMPLES 58–84

Using the general procedure of Example 4, the following instant compounds of formula IV are prepared.

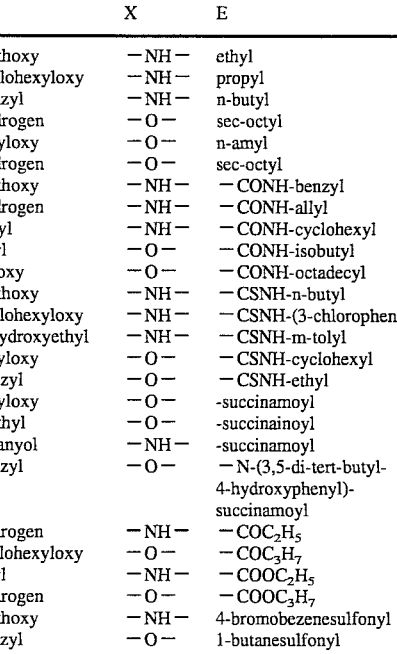

| Example | R₁ | X | E |
|---|---|---|---|
| 58 | methoxy | —NH— | ethyl |
| 59 | cyclohexyloxy | —NH— | propyl |
| 60 | benzyl | —NH— | n-butyl |
| 61 | hydrogen | —O— | sec-octyl |
| 62 | octyloxy | —O— | n-amyl |
| 63 | hydrogen | —O— | sec-octyl |
| 64 | methoxy | —NH— | —CONH-benzyl |
| 65 | hydrogen | —NH— | —CONH-allyl |
| 66 | butyl | —NH— | —CONH-cyclohexyl |
| 67 | allyl | —O— | —CONH-isobutyl |
| 68 | ethoxy | —O— | —CONH-octadecyl |
| 69 | methoxy | —NH— | —CSNH-n-butyl |
| 70 | cyclohexyloxy | —NH— | —CSNH-(3-chlorophenyl) |
| 71 | 2-hydroxyethyl | —NH— | —CSNH-m-tolyl |
| 72 | octyloxy | —O— | —CSNH-cyclohexyl |
| 73 | benzyl | —O— | —CSNH-ethyl |
| 74 | octyloxy | —O— | -succinamoyl |
| 75 | methyl | —O— | -succinainoyl |
| 76 | ethanyol | —NH— | -succinamoyl |
| 77 | benzyl | —O— | —N-(3,5-di-tert-butyl-4-hydroxyphenyl)-succinamoyl |
| 78 | hydrogen | —NH— | —COC₂H₅ |
| 79 | cyclohexyloxy | —O— | —COC₃H₇ |
| 80 | allyl | —NH— | —COOC₂H₅ |
| 81 | hydrogen | —O— | —COOC₃H₇ |
| 82 | methoxy | —NH— | 4-bromobezenesulfonyl |
| 83 | benzyl | —O— | 1-butanesulfonyl |

What is claimed is:

1. A compound which is an azo derivative of formula IV

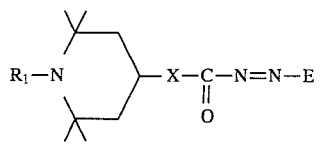

where

R₁ is hydrogen, oxyl, hydroxyl, alkyl of 1 to 8 carbon atoms, alkyl of 2 to 4 carbon atoms substituted by one hydroxyl group, allyl, benzyl, benzyl substituted by one of two alkyl of 1 to 4 carbon atoms, alkoxy of 1 to 18 carbon atoms, cycloalkoxy of 5 to 12 carbon atoms or alkanoyl of 1 to 8 carbon atoms;

X is —O— or —NR₂— where R₂ is hydrogen, alkyl of 1 to 18 carbon atoms, cycloalkyl of 5 to 12 carbon atoms, phenylalkyl of 7 to 15 carbon atoms, alkyl of 2 to 4 carbon atoms substituted by one alkoxy group of 1 to 12 carbon atoms or a group of formula II

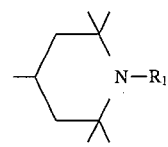

in which R₁ is as defined above; and

E is alkyl of 1 to 20 carbon atoms, cycloalkyl of 5 to 12 carbon atoms, aryl of 6 to 14 carbon atoms or phenylalkyl of 7 to 22 carbon atoms, or E is —CONHR₄, —CSNHR₅, —COR₆COR₇, —COR₈CONHR₉, —COR₁₀, —COOR₁₁ or —SO₂R₁₂, in which R₄, R₅, R₇, R₉, R₁₀, R₁₁ and R₁₂ are each independently of the other hydrogen, alkyl of 1 to 20 carbon atoms, cycloalkyl of 5 to 12 carbon atoms, aryl of 6 to 14 carbon atoms or phenylalkyl of 7 to 22 carbon atoms; and R₆ and R₈ are each independently of the other an alkylene of 1 to 12 carbons.

2. A stabilized polymer composition which comprises (a) a polymer, copolymer or polymer blend which contains in at least one polymer or polymer component significant ethylenic unsaturation, and (b) an effective stabilizing amount of an asymmetrical azo derivative grafted to said polymer or polymer component, said derivative having before grafting the structure of formula IV

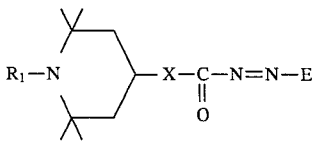

where

R₁ is hydrogen, oxyl, hydroxyl, alkyl of 1 to 8 carbon atoms, alkyl of 2 to 4 carbon atoms substituted by one hydroxyl group, allyl, benzyl, benzyl substituted by one of two alkyl of 1 to 4 carbon atoms, alkoxy of 1 to 18 carbon atoms, cycloalkoxy of 5 to 12 carbon atoms or alkanoyl of 1 to 8 carbon atoms;

X is —O— or —NR₂— where R₂ is hydrogen, alkyl of 1 to 18 carbon atoms, cycloalkyl of 5 to 12 carbon atoms, phenylalkyl of 7 to 15 carbon atoms, alkyl of 2 to 4 carbon atoms substituted by one alkoxy group of 1 to 12 carbon atoms or a group of formula II

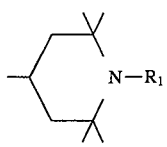

in which $R_1$ is as defined above; and

E is a alkyl of 1 to 20 carbon atoms, cycloalkyl of 5 to 12 carbon atoms, aryl of 6 to 14 carbon atoms or phenylalkyl of 7 to 22 carbon atoms, or E is —$CONHR_4$, —$CSNHR_5$, —$COR_6COR_7$, —$COR_8CONHR_9$, —$COR_{10}$, —$COOR_{11}$ or —$SO_2R_{12}$, in which $R_4$, $R_5$, $R_7$, $R_9$, $R_{10}$, $R_{11}$ and $R_{12}$ are each independently of the other hydrogen, alkyl of 1 to 20 carbon atoms, cycloalkyl of 5 to 12 carbon atoms, aryl of 6 to 14 carbon atoms or phenylalkyl of 7 to 22 carbon atoms; and $R_6$ and $R_8$ are each independently of the other an alkylene of 1 to 12 carbons.

3. A composition according to claim 2 wherein component (a) is a polymer, copolymer or polymer blend, having significant ethylenic unsaturation in at least one polymer or polymer component, selected from the group consisting of ABS, HIPS, emulsion SBR, PP/EPDM, PP/NBR, PP/NR, ABS/PC, ABS/nylon, ABS/PVC, ABS/polyester, ABS/SMA, ABS/polysulfone, ASA/PC, acetal/elastomer, polyester/elastomer, nylon/elastomer, PPO/NR, EPDM/NBR and EPDM/olefin.

4. A composition according to claim 3 wherein component (a) is ABS or ABS/PC.

5. A compound of formula IV according to claim 1, wherein E is an alkyl of 1 to 12 carbon atoms, cycloalkyl of 5 to 8 carbon atoms, phenyl or phenylalkyl of 7 to 14 carbon atoms.

6. A compound of formula IV according to claim 1, wherein E is alkyl of 1 to 10 carbon atoms, cyclohexyl, phenyl or phenylalkyl of 7 to 9 carbon atoms.

7. A compound of formula IV according to claim 1, wherein E is —$CONHR_4$ or —$CSNHR_5$ and $R_4$ and $R_5$ are each independently of the other alkyl of 1 to 12 carbon atoms, cycloalkyl of 5 to 8 carbon atoms, phenyl or phenylalkyl of 7 to 14 carbon atoms.

8. A compound of formula IV according to claim 1, wherein E is —$CONHR_4$ or —$CSNHR_5$ and $R_4$ and $R_5$ are each independently of the other alkyl of 1 to 10 carbon atoms, cyclohexyl, phenyl or phenylalkyl of 7 to 9 carbon atoms.

9. A compound of formula IV according to claim 1, wherein E is —$COR_6COR_7$ or —$COR_8CONHR_9$ and $R_6$ and $R_8$ are each independently of the other alkylene of 1 to 8 carbon atoms and $R_7$ and $R_9$ are each independently of the other alkyl of 1 to 8 carbon atoms, cycloalkyl of 5 to 8 carbon atoms, aryl of 6 to 12 carbon atoms or phenylalkyl of 7 to 14 carbon atoms.

10. A compound of formula IV according to claim 1, wherein E is —$COR_{10}$ and $R_{10}$ is alkyl of 1 to 12 carbon atoms, cycloalkyl of 5 to 8 carbon atoms, phenyl or phenylalkyl of 7 to 14 carbon atoms.

11. A compound of formula IV according to claim 1, wherein E is —$COOR_{11}$ or —$SO_2R_{12}$ and $R_{11}$ and $R_{12}$ are each independently of the other alkyl of 1 to 8 carbon atoms, cycloalkyl of 5 to 8 carbon atoms, aryl of 6 to 12 carbon atoms or phenyl alkyl of 7 to 14 carbon atoms.

12. A compound of formula IV according to claim 1, wherein $R_1$ is alkyl of 1 to 4 carbon atoms, alkyl of 2 or 3 carbon atoms substituted by one hydroxyl group, alkoxy of 1 to 12 carbon atoms, cycloalkoxy of 5 or 6 carbon atoms or alkanoyl of 1 to 4 carbon atoms.

13. A compound of formula IV according to claim 1, wherein $R_1$ is methyl, 2-hydroxyethyl, methoxy, heptyloxy, octyloxy, cyclohexyloxy, formyl or acetyl.

14. A compound of formula IV according to claim 1, wherein X is —O— or —$NR_2$— where $R_2$ is hydrogen, butyl or dodecyl or a group of formula II.

15. A compound of formula IV according to claim 1, wherein X is —O—.

* * * * *